United States Patent
Grindrod et al.

(10) Patent No.: US 12,357,650 B2
(45) Date of Patent: *Jul. 15, 2025

(54) METHODS AND COMPOSITIONS FOR CANCER THERAPIES THAT INCLUDE DELIVERY OF HALOGENATED THYMIDINES AND THYMIDINE PHOSPHORLYLASE INHIBITORS IN COMBINATION WITH RADIATION

(71) Applicant: Shuttle Pharmaceuticals, Inc., Rockville, MD (US)

(72) Inventors: Scott Grindrod, Rockville, MD (US); Mira Jung, Rockville, MD (US); Olga Timofeeva, Rockville, MD (US); Milton Brown, Rockville, MD (US); Anatoly Dritschilo, Rockville, MD (US)

(73) Assignee: Shuttle Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/528,550

(22) Filed: Dec. 4, 2023

(65) Prior Publication Data

US 2024/0226129 A1    Jul. 11, 2024

Related U.S. Application Data

(63) Continuation of application No. 18/194,648, filed on Apr. 2, 2023, now abandoned, which is a continuation of application No. 16/475,999, filed as application No. PCT/US2018/012914 on Jan. 9, 2018, now Pat. No. 11,654,157.

(60) Provisional application No. 62/444,155, filed on Jan. 9, 2017.

(51) Int. Cl.
*A61K 31/7072* (2006.01)
*A61K 31/513* (2006.01)
*A61K 33/243* (2019.01)

(52) U.S. Cl.
CPC ........ *A61K 31/7072* (2013.01); *A61K 31/513* (2013.01); *A61K 33/243* (2019.01); *A61K 2121/00* (2013.01)

(58) Field of Classification Search
None
See application file for complete search history.

(56) References Cited

U.S. PATENT DOCUMENTS

| | | | |
|---|---|---|---|
| 5,728,684 A | 3/1998 | Cheng et al. | |
| 5,744,475 A | 4/1998 | Yano et al. | |
| 6,159,969 A | 12/2000 | Yano et al. | |
| 6,294,535 B1 | 9/2001 | Yano et al. | |
| 6,479,500 B1 | 11/2002 | Fukushima et al. | |
| 7,799,783 B2 | 9/2010 | Emura et al. | |
| 2008/0161292 A1 | 7/2008 | Giranda et al. | |
| 2010/0135983 A1 | 6/2010 | Hyde et al. | |
| 2011/0065663 A1 | 3/2011 | Balzarini | |
| 2012/0010165 A1 | 1/2012 | Fukushima | |
| 2016/0257649 A1 | 9/2016 | Grindrod et al. | |

FOREIGN PATENT DOCUMENTS

| | | | |
|---|---|---|---|
| WO | 20090138507 A2 | 11/2009 | |
| WO | 2016044690 A1 | 3/2016 | |
| WO | 2016105518 A1 | 6/2016 | |

OTHER PUBLICATIONS

Aschele et al., Primary tumor response to preoperative chemoradiation with or without oxaliplatin in locally advanced rectal cancer: pathologic results of the STAR-01 randomized phase III trial. J Clin Oncol. 2011;29(20):2773-80.
Berry et al., Selective radiosensitization of drug-resistant MutS homologue-2 (MSH2) mismatch repair-deficient cells by halogenated thymidine (dThd) analogues: Msh2 mediates dThd analogue DNA levels and the differential cytotoxicity and cell cycle effects of the dThd analogues and 6-thioguanine. Cancer research. Oct. 15, 2000;60(20):5773-5780.
Berry et al., The mismatch repair protein, hMLHI, mediates 5-substituted halogenated thymidine analogue cytotoxicity, DNA incorporation, and radiosensitization in human colon cancer cells. Cancer research. Apr. 15, 1999;59(8):1840-1845.
Chang et al., A phase I study of intraarterial iododeoxyuridine in patients with colorectal liver metastases. J Clin Oncol. May 1989;7(5):662-668.
Chi et al. Iododeoxyuridine Chemosensitization of cis-Diamminedichloroplatinum(II) in Human Bladder Cells. Cancer Research. May 15, 1994; 54:2701-2706.
Eisbruch et al., Bromodeoxyuridine alternating with radiation for advanced uterine cervix cancer: a phase I and drug incorporation study. J Clin Oncol. Jan. 1999;17(I):31-40.
Epstein et al., Treatment of locally advanced cancer of the head and neck with 5'-iododeoxyuridine and hyperfractionated radiation therapy: measurement of cell labeling and thymidine replacement. Journal of the National Cancer Institute. Dec. 7, 1994;86(23): 1775-1780.
European Office Action, dated Aug. 24, 2022, for the corresponding EP patent application No. 18736185.2, 6 pages.
Extended European Search Report dated Oct. 30, 2020 for European Patent Application No. EP 18736185, 7 pages.
Fink et al., The role of DNA mismatch repair in drug resistance. Clin Cancer Res. Jan. 1998;4(I): 1-6.
Fornace et al., Enhancement of radiation damage in cellular DNA following unifilar substitution with iododeoxyuridine. International journal of radiation oncology, biology, physics. Apr. 1990;18(4):873-878.
Gerard et al., Comparison of two neoadjuvant chemoradiotherapy regimens for locally advanced rectal cancer: results of the phase III trial ACCORD 12/0405—Prodige 2. J Clin Oncol. 2010;28(10): 1638-44.

(Continued)

*Primary Examiner* — Dale R Miller
(74) *Attorney, Agent, or Firm* — Morgan, Lewis & Bockius LLP

(57) ABSTRACT

Methods and formulations are provided for treating cancer and neoplastic diseases in conjunction with radiation therapy where such methods and formulations include a combination of a radiosensitizing agent that is metabolized by thymidine phosphorylase and a thymidine phosphorylase inhibitor that increases the half-life of the radiosensitizing agent.

14 Claims, 8 Drawing Sheets

(56) References Cited

OTHER PUBLICATIONS

Groves et al., A phase II trial of high-dose bromodeoxyuridine with accelerated fractionation radiotherapy followed by procarbazine, lomustine, and vincristine for glioblastoma multiforme. International journal of radiation oncology, biology, physics. Aug. 1, 1999;45(1): 127-135.
International Search Report for Application PCT/US2018/012914 dated Mar. 5, 2018.
International Preliminary Report on Patentability for Application PCT/US2018/012914 dated Mar. 5, 2018.
Kinsella, An approach to the radiosensitization of human tumors. Cancer J Sci Am. Jul-Aug. 1996;2(4): 184-193.
Kinsella, Coordination of DNA mismatch repair and base excision repair processing of chemotherapy and radiation damage for targeting resistant cancers. Clin Cancer Res. Mar. 15, 2009; 15(6): 1853-1859.
Kinsella et al., Enhancement of X ray induced DNA damage by pre-treatment with halogenated pyrimidine analogs. International journal of radiation oncology, biology, physics. May 1987;13(5):733-739.
Kinsella, Update on radiosensitization by halogenated thymidine analogs-molecular mechanisms of drug processing and cell death signaling: implications for future clinical trials. Cancer Biol Ther. Oct. 2008;7(10): 1567-1569.
Knol et al., Incorporation of 5-bromo-2'- deoxyuridine into colorectal liver metastases and liver in patients receiving a 7-day hepatic arterial infusion. Cancer research. Sep. 1, 1995;55(17):3687-3691.
Krishnamurthi et al., Adjuvant therapy for rectal cancer. Clin Colon Rectal Surg. 2007;20(3): 167-81. PMCID: 2789506.
Lawrence et al., The dependence of halogenated pyrimidine incorporation and radiosensitization on the duration of drug exposure. International journal of radiation oncology, biology, physics. Jun. 1990;18(6): 1393-1398.
Lawrence et al., The effect of single versus double-strand substitution on halogenated pyrimidine-induced radiosensitization and DNA strand breakage in human tumor cells. Radiation research. Aug. 1990;123(2): 192-198.
McGinn et al. Leucovorin modulation of 5-iododeoxyuridine radiosensitization: a phase I study. Clin Cancer Res. Aug. 1996;2(8): 1299-1305.
Prados et al., Influence of bromodeoxyuridine radiosensitization on malignant glioma patient survival: a retrospective comparison of survival data from the Northern California Oncology Group (NCOG) and Radiation Therapy Oncology Group trials (RTOG) for glioblastoma multiforme and anaplastic astrocytoma. International journal of radiation oncology, biology, physics. Feb. 1, 1998;40(3):653-659.
Rodel et al., Preoperative chemoradiotherapy and postoperative chemotherapy with fluorouracil and oxaliplatin versus fluorouracil alone in locally advanced rectal cancer: initial results of the German CAO/ARO/AIO-04 randomised phase 3 trial. Lancet Oncol. 2012;13(7):679-87.
Rodriguez et al., Kinetics of cell labeling and thymidine replacement after continuous infusion of halogenated pyrimidines in vivo. International journal of radiation oncology, biology, physics. Apr. 30, 1994;29(1): 105-113.
Roh et al. The impact of capecitabine and oxaliplatin in the preoperative multimodality treatment in patients with carcinoma of the rectum: NSABP R-04. Journal of Clinical Oncology. 2011;29(15).
D Santi: "Perspective Perspectives on the Design and Biochemical Pharmacology of Inhibitors of Thymidylate Synthetase", Journal of Medicinal Chemistry, vol. 23, No. 2, Feb. 1, 1980 (Feb. 1, 1980), pp. 103-111.
Schulz et al., Continuous 28-day iododeoxyuridine infusion and hyperfractionated accelerated radiotherapy for malignant glioma: a phase I clinical study. International journal of radiation oncology, biology, physics. Jul. 15, 2004;59(4): 1107-1115.
Seo et al., Differential radiosensitization in DNA mismatch repair-proficient and -deficient human colon cancer xenografts with 5-iodo-2-pyrimidinone-2'-deoxyribose. Clin Cancer Res. Nov. 15, 2004;10(22):7520-7528.
Shewach et al., Antimetabolite radiosensitizers. J Clin Oncol. Sep. 10, 2007;25(26):4043-4050.
Speth et al., Fluorodeoxyuridine modulation of the incorporation of iododeoxyuridine into DNA of granulocytes: a phase I and clinical pharmacological study. Cancer research. May 15, 1988;48(10):2933-2937.
Torrence P F; The Chemistry and Biochemistry of Purine and Pyrimidine Nucleoside Antiviral and Antitumor Agents; Drugs and the Pharmaceutical Sciences, Dekker, New York, NY, US, vol. 24, Jan. 1, 1984 (Jan. 1, 1984), pp. 113-176.
Urtasun et al., Survival improvement in anaplastic astrocytoma, combining external radiation with halogenated pyrimidines: final report of RTOG 86-12, Phase I-II study. International journal of radiation oncology, biology, physics. Dec. 1, 1996;36(5): 1163-1167.
Vallerga et al., New radiosensitizing regimens, drugs, prodrugs, and candidates. Clin Adv Hematol Oncol. 2004;2(12):793-805.
Written Opinion of the International Search Authority for Application PCT/US2018/012914 dated Mar. 5, 2018.
Emura, T., Suzuki, N., Fujioka, A., Ohshimo, H., & Fukushima, M. (2005). Potentiation of the antitumoractivityofa, a, a-trifluorothymidine by the co-administration of an inhibitor of thymidine phosphorylase at a suitable molar ratio in vivo. International journal of oncology, 27(2), 449-455. (Year: 2005).
El-Naggar, M., Ebbing, E., Bijnsdorp, I., van den Berg, J., & Peters, G. J. (2014). Radiosensitization by thymidine phosphorylase inhibitor in thymidine phosphorylase negative and overexpressing bladder cancer cell lines. Nucleosides, Nucleotides and Nucleic Acids, 33(4-6), 413-421. (Year: 2014).
Fukushima, M., Suzuki, N., Emura, T., Yano, S., Kazuno, H., Tada, Y., . . . & Asao, T. (2000). Structure and activity of specific inhibitors of thymidine phosphorylase to potentiate the function of antitumor 2'-deoxyribonucleosides. Biochemical pharmacology, 59(10), 1227-1236. (Year: 2000).
Communication pursuant to Article 94(3) EPC issued in corresponding European Patent Application No. 18736185.2, dated Sep. 27, 2024, 12 pages.

METHODS AND COMPOSITIONS FOR CANCER THERAPIES THAT INCLUDE DELIVERY OF HALOGENATED THYMIDINES AND THYMIDINE PHOSPHORLYASE INHIBITORS IN COMBINATION WITH RADIATION

CROSS REFERENCE TO RELATED APPLICATIONS

This application is a Continuation of U.S. patent application Ser. No. 18/194,648, filed Apr. 2, 2023, which is a Continuation of U.S. patent application Ser. No. 16/475,999, filed Jul. 3, 2019, now U.S. Pat. No. 11,654,157, which is the U.S. National Stage of International Patent Application No. PCT/US2018/012914, filed Jan. 9, 2018 which claims the benefit of U.S. Provisional Application No. 62/444,155, filed Jan. 9, 2017, the entirety of which are incorporated herein by reference.

GOVERNMENT LICENSE RIGHTS

This invention was made with government support under grant No. HHSN261201400 013C awarded by the National Institutes of Health (SBIR Program). The government has certain rights in the invention.

FIELD OF THE INVENTION

The application relates generally to methods of using radiosensitizing agents that are metabolized by thymidine phosphorylase for treating disease and more particularly, but not exclusively, to methods of treating cancer by administering 5-iodo-2'-deoxyuridine (IUdR) to a patient in combination with a thymidine phosphorylase inhibitor (TPI) and radiation therapy.

BACKGROUND OF THE INVENTION

Administering radiation sensitizers in combination with radiation therapy can improve cancer treatment outcomes. 5-iodo-2'-deoxyuridine (IUdR) has been demonstrated as a potent radiation sensitizer in preclinical and clinical studies. The effectiveness of radiation sensitization is directly proportional to the amount of IUdR that is incorporated into cancer cell DNA. However, IUdR drug levels in plasma following oral delivery are insufficient to achieve effective levels of radiation sensitization due to IUdR degradation by the thymidine phosphorylase enzyme in the gut and in the liver.

Accordingly, there is a need in the field for treatment options that include radiation sensitization involving IUdR that allow for the protection of IUdR from degradation and early metabolization. The invention disclosed herein meets this need.

SUMMARY OF THE INVENTION

The application provides methods and formulations directed to treating cancer that involve sensitizing cancer and/or neoplastic cells with a radiosensitizing agent (e.g., IUdR) while additionally providing a thymidine phosphorylase inhibitor (TPI) that prevents degradation of the radiosensitizing agent. For example, inhibiting thymidine phosphorylase activity may increase plasma levels of IUdR in a patient, thereby resulting in increased IUdR incorporation into cancer cell DNA and greater radiation sensitization.

In a first aspect, the invention includes a method for sensitizing cancer cells in a patient having cancer to radiation therapy. The method may include a step of administering a therapeutically effective amount of a radiosensitizing agent that is metabolized by thymidine phosphorylase to the patient to thereby sensitize the cancerous cells to radiation. Moreover, the radiosensitizing agent may include 5-iodo-2'-deoxyuridine (IUdR) or a prodrug thereof. The method may also include a step of administering a selected effective amount of a thymidine phosphorylase inhibitor to the patient that is configured to inhibit thymidine phosphorylase to thereby hinder metabolization of the radiosensitizing agent by thymidine phosphorylase.

In another aspect, the invention includes a method for treating cancer in a patient in need of such treatment by irradiating cancerous cells in the patient. The method may include the step of administering a therapeutically effective amount of a radiosensitizing agent that is metabolized by thymidine phosphorylase to the patient to sensitize cancerous cells to radiation. The radiosensitizing agent may include 5-iodo-2'-deoxyuridine (IUdR) or a prodrug thereof. Moreover, the method may include the step of administering a selected effective amount of a thymidine phosphorylase inhibitor to the patient that is configured to inhibit thymidine phosphorylase to hinder metabolization of the radiosensitizing agent by thymidine phosphorylase. Additionally, the method may include irradiating a selected tissue of the patient that includes the cancerous cells that are sensitized to radiation therapy by the radiosensitizing agent.

In some embodiments, the thymidine phosphorylase inhibitor used in the methods described herein may include Tipiracil.

The cancers treated by the methods described herein, and associated cancerous cells and tissues, may include one or more of pancreatic cancer, hepatic cancer, prostate cancer, colorectal cancer, breast cancer, gastric cancer, non-small-cell lung cancer, metastatic breast cancer, head and neck cancers, endometrial cancer, ovarian cancer, ureter cancer, cervical cancer, esophageal cancer, bladder cancer, small-cell cancer, non-small-cell cancer, malignant lymphomas, brain cancer, rectal cancer, and sarcomas. In certain embodiments, the cancer may be rectal cancer or brain cancer. Additionally, the cancer may be a pediatric cancer selected from the group consisting of leukemia, lymphoma, Hodgkin's disease, rhabdomyosarcoma, Ewing's sarcoma, osteosarcoma, dysgerminomas, Wilm's tumor, retinoblastoma, ependymoma, and medulloblastoma.

In other embodiments of the invention, the radiosensitizing agent is IUdR. Furthermore, the prodrug of IUdR, 5-iodo-2-pyrimidinone-2'-deoxyribose (IPdR), may be used.

In another aspect, the invention includes a kit for providing a method for treating cancer in a patient in need of such treatment by irradiating cancerous cells in the patient. The kit may include 5-iodo-2'-deoxyuridine (IUdR) or a prodrug thereof. The kit may also include a thymidine phosphorylase inhibitor such as, for example, Tipiracil. In addition, the kit may include instructions for use of IUdR or a prodrug thereof and the thymidine phosphorylase inhibitor in combination with radiation therapy for treating cancer in the patient in need of such treatment.

In a further aspect, the invention includes a pharmaceutical composition for sensitizing cancerous cells to radiation. The composition may include a radiosensitizing agent that is metabolized by thymidine phosphorylase. Specifically, the radiosensitizing agent may include 5-iodo-2'-deoxyuridine (IUdR) or a prodrug thereof. Moreover, the composition may include a thymidine phosphorylase inhibitor that prevents the metabolism of the radiosensitizing agent by thymidine phosphorylase. The composition may also include one or more physiologically compatible carrier mediums.

In certain embodiments, the thymidine phosphorylase inhibitor may include Tipiracil. Moreover, the physiologically compatible carrier medium may include one or more of a solvent, diluent, liquid vehicle, dispersion aid, suspension aid, surface agent, isotonic agent, thickening agent, emulsifying agent, preservative, solid binder, lubricant, and filler.

BRIEF DESCRIPTION OF THE DRAWINGS

The foregoing summary and the following detailed description of the exemplary embodiments described herein may be further understood when read in conjunction with the appended drawings, in which:

FIG. 2C illustrates a log-linear plot of the means of FIGS. 2A and 2B. Compound A=IUdR, Compound B=Tipiracil.

FIG. 3C illustrates a log-linear plot of the means of FIGS. 3A and 3B. Compound A=IUdR, Compound B=Tipiracil.

DETAILED DESCRIPTION OF THE INVENTION

Radiation therapy (RT) is an effective modality for the treatment of cancers. Strategies to improve the therapeutic index of RT have been focused on precise targeting of the tumors to deliver a sufficient radiation dose to control the tumor while limiting doses to normal tissues to reduce undesirable side effects.

The therapeutic index of RT can be improved by using agents with radiation sensitizing properties. Cytotoxic chemotherapeutic agents that enhance the killing effects of RT when given concomitantly with RT include 5-fluorouracil (5-FU), capecitabine (an oral 5-FU prodrug), cisplatinum, oxaliplatinum, and, to a lesser extent, mitomycin-C, gemcitabine, taxol, and temozolomide, as well as some biologics. However, these cytotoxic agents have their own single agent toxicities: the antimetabolites, 5-FU and capecitabine toxicities include myelosuppression, oral mucositis, vomiting, diarrhea, fatigue, and hand-foot syndrome. Oxaliplatinum added to 5-FU and RT enhance normal tissue toxicities, which include peripheral neuropathy and fatigue.

Figure 1:
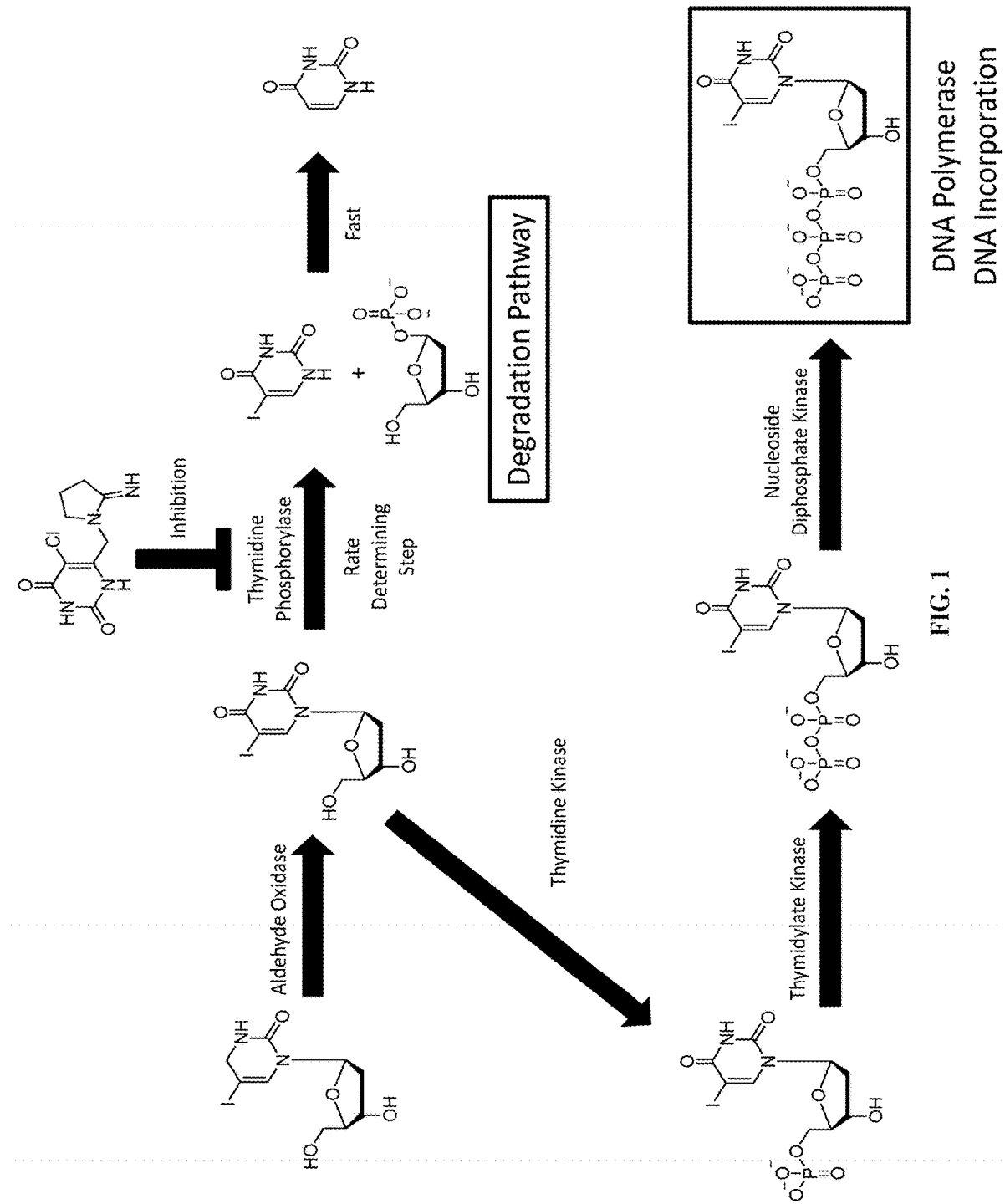
FIG. 1 diagrammatically illustrates the separate biological pathways of IUdR in vivo that lead to degradation or DNA incorporation, which results in radiosensitizing activity.

The halogenated thynidine (TdR) analogs, bromodeoxyuridine (BUdR) and iododeoxyuridine (IUdR), for example, are a class of pyrimidine analogs that have been recognized as potential radiosensitizing agents since the early 1960s. As shown in FIG. 1, their cellular uptake and metabolism are dependent on the TdR salvage pathway where they are initially phosphorylated to the monophosphate derivative by the rate-limiting enzyme, thymidine kinase (TK). After sequential phosphorylation to triphosphates, they are then used in DNA replication, in competition with deoxythymidine triphosphate (dTTP), by DNA polymerase. Indeed, DNA incorporation is a prerequisite for radiosensitization of human tumors by the halogenated TdR analogs, and the extent of radiosensitization correlates directly with the percentage TdR replacement in DNA. Without being limited to any one theory of activity, the molecular mechanisms of radiosensitization are most likely related to the increased susceptibility of TdR analog-substituted DNA to the generation of highly reactive uracil free radicals by ionizing radiation (IR), which may also damage unsubstituted complementary-strand DNA. Pre-IR exposure to TdR analogs may also reduce cellular repair of IR damage.

Halogenated TdR analogs represent viable radiosensitizers in cancer treatment strategies that include radiation therapy. However, the TdR analogs may be rapidly metabolized in both rodents and humans, principally with cleavage of deoxyribose and subsequent dehalogenation by hepatic and extrahepatic metabolism, when given as a bolus infusion with a plasma half-life of <5 min. Consequently, prolonged continuous or repeated intermittent drug infusions over several weeks before and during irradiation are necessary, based on in vivo human tumor kinetics, to maximize the proportion of tumor cells that incorporate TdR analogs during the S phase of the cell cycle. Phase I and II trials using prolonged continuous or repeated intermittent intravenous infusions of BUdR or IUdR before and during radiation therapy have focused principally on patients with high-grade brain tumors. These clinically radioresistant tumors can have a rapid proliferation rate (potential tumor doubling times of 5-15 days) and are surrounded by non-proliferating normal brain tissues that show little to no DNA incorporation of the TdR analogs. As such, high-grade brain tumors are ideal targets for this approach to radiosensitization.

The results of Phase I/II clinical trials suggest an improved outcome compared to radiation therapy alone in patients with anaplastic astrocytomas and possibly in patients with glioblastoma multiforme. A therapeutic gain in clinical radiosensitization using halogenated TdR analogs may also exist for other types of poorly radioresponsive (radioresistant) cancers, including locally advanced cervical cancer, head and neck cancers, unresectable hepatic metastases from colorectal cancers, and locally advanced sarcomas, based on Phase I/II clinical trials. However, systemic toxicity to rapidly proliferating normal tissues (principally bone marrow and intestine) can limit the duration and dose rate of the drug infusion and consequently may limit the extent of human tumor radiosensitization. Indeed, the use of high dose, short (96 h), intermittent intravenous infusions of BUdR can result in significant systemic myelosuppressive and dermatological toxicities.

Various pharmacological approaches have been attempted experimentally and clinically to improve the therapeutic gain of halogenated TdR analog radiosensitization in poorly radioresponsive (or clinically radioresistant) human tumors. The use of selective intra-arterial infusions, to thereby increase tumor bed drug concentrations, has been used clinically for primary brain tumors and hepatic metastases with a modest improvement in therapeutic gain. Experimentally, biochemical modulation of the key enzymes involved in TdR analog metabolism (e.g., TK) or in the maintenance of cellular deoxyribonucleotide triphosphate pools (both thymidylate synthase and ribonucleotide reductase) have been studied using in vitro and in vivo human tumor systems. Biochemical modulation of thymidylate synthase has also been attempted in clinical Phase I trials using concomitant continuous infusions of IUdR with either fluorodeoxyuridine (FUdR) or folinic acid (leucovorin), but no significant improvements in the therapeutic gain for radiosensitization were found compared to IUdR infusions alone.

Regarding the mechanism of radiation therapy, cells die as a result of irreversible DNA strand breaks caused by irradiation, which interfere with cell division and proliferation. Nucleoside analogs, such as 5-iodo-2'-deoxyuridine (IUdR) and 5-bromo-2'-deoxyuridine (BUdR), are agents that "falsely" incorporate into DNA to render cells more susceptible to the lethal effects of RT by two-three fold, as compared to cells without the defective DNA. The magnitude of radiosensitization correlates directly with the % IUdR-DNA cellular replacement. Determination of % IUdR-DNA incorporation can serve as a radiosensitization biomarker. Additionally, in a small series of patients with head and neck cancers or liver metastases from colorectal cancer, the % IUdR-DNA incorporation in tumors ranged to 5%, but was less than 1% in adjacent normal tissue, further supporting a therapeutic window for IUdR-mediated radiosensitization. Although IUdR has clear potential as a clinically active radiosensitizer, its development has been limited by the need for prolonged ci (intra-arterial or intravenous), before and during RT, to radiosensitize tumors. Prolonged ci of IUdR resulted in myelosuppression and acute GI toxicities, limiting the tolerated doses and the potential for clinical radiosensitization. However, the invention maximizes the potential of radiosensitizing agents, such as IUdR, in sensitizing cancerous cells and tissues to radiation by reducing metabolic degradation during treatment.

As described above, IUdR is a radiation sensitizer with a short plasma half-life ($T_{1/2}$) In the field, this requires drug delivery by continuous infusion to achieve and maintain the necessary therapeutic levels. By combining IUdR with a thymidine phosphorylase inhibitor, the plasma $T_{112}$ may be increased to improve IUdR incorporation into DNA and enhance the radiation sensitization of cancers.

Tipiracil, an exemplary TPI, prevents a,a,a-trifluorothymidine (FTD) degradation, enabling higher blood concentrations of FTD while allowing for oral administration of the combination of an anticancer therapeutic that includes FTD and TPI (i.e., TAS102) in a molar ratio of 1:0.5. See, e.g., U.S. Pat. Nos. 5,744,475, 6,479,500, and 7,799,783; the entireties of which are incorporated herein by reference.

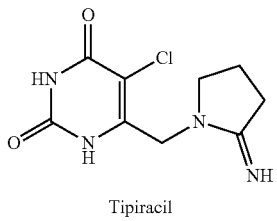 [SMILES: N=C1CCCN1Cc1[nH]c(=O)[nH]c(=O)c1Cl]

Tipiracil

The potent radiosensitizer IUdR lacks single agent efficacy as an anticancer agent. Moreover, IUdR's commercialization has been limited by its short $T_{1/2}$ in plasma, requiring constant infusion delivery, and the associated hematologic and GI toxicities. As set forth herein, enzymatic degradation of IUdR may be limited by the additional delivery of a TPI with IUdR, thereby resulting in the: (1) increased efficacy of radiation therapy; and (2) reduced toxicity by avoiding constant infusion delivery. Additionally, by delivering IUdR in a formulation with TPI, IUdR degradation in the gut will also be attenuated, permitting oral delivery of a combination drug formulation.

Accordingly, IUdR and a TPI can be delivered orally to patients prior to radiation therapy in separate drug dosages, as a single combination drug preparation, or as a rapid IV infusion. Inhibition of IUdR metabolism will lead to increased bioavailability for incorporation into cancer DNA and enhanced cellular response to ionizing radiation.

Regarding the invention more broadly, the invention includes methods and formulations for treating cancer in a patient that may be in need of such treatment, which may preliminarily include sensitizing cancerous cells and tissues to radiation therapy. Generally, the methods described herein may include the administration of a radiosensitizing agent and a thymidine phosphorylase inhibitor (TPI). The administration of the radiosensitizing agent and the TPI may be followed by the application of radiation therapy. Radiation sensitizing agents may be defined as compounds that sensitize cancerous or neoplastic cells to radiation therapy. Moreover, the methods described herein may include the administration of a radiomimetic therapeutic agent in addition to the application of radiation therapy.

The term "neoplastic disease" refers to a proliferative disorder caused or characterized by the proliferation of cells, which are unrestrained by normal growth control. The term "cancer" includes benign and malignant tumors and any other proliferative disorders (e.g., the formation of metastasis). Cancers of the same tissue type in general originate from the same tissue, and are for example divided into different subtypes based on their biological characteristics. Specific examples of cancers that may be treated by the methods and compositions described herein include solid tumors and may include pancreatic cancer, prostate cancer, hepatic cancer, colorectal cancer, breast cancer, gastric cancer, non-small-cell lung cancer, metastatic breast cancer, head and neck cancers, endometrial cancer, ovarian cancer, ureter cancer, cervical cancer, esophageal cancer, bladder cancer, ovarian cancer, small-cell cancer and non-small cell cancer, malignant lymphomas, brain cancer (e.g, malignant glioma), sarcomas, and rectal cancer. In certain aspects, the methods described herein pertain to treatments for brain cancer and rectal cancer.

As used herein, the terms "administer," "administration" or "administering" refer to (1) providing, giving, dosing, and/or prescribing by either a health practitioner or his authorized agent or under his or her direction according to the disclosure; and (2) putting into, taking, or consuming by the patient or person himself or herself, according to the disclosure.

As used herein, the terms "treat," "treatment," and/or "treating" may refer to the management of a disease, disorder, or pathological condition (e.g., cancer or neoplastic disorder) with the intent to cure, ameliorate, stabilize, prevent, or control of the disease, disorder, or pathological condition. Regarding control of the disease, disorder, or pathological condition more specifically, "control" may include the absence of disease progression, as assessed by the response to the methods recited herein, where such response may be complete (e.g., placing the disease in remission) or partial (e.g., slowing the spread of cancerous cells and tissues and/or preventing, slowing, or halting metastasis). For example, a patient responding to the methods of treatment disclosed herein may exhibit the absence of disease progression (e.g., halting the growth and/or spread of neoplastic cells and tissues) over another patient that does not receive the methods of treatment described herein.

Following treatment, if no detectable evidence of residual cancer is found in a tissue sample, the response to treatment may be considered a "pathologic complete response" or "pCR."

In accordance with the invention, the methods may include the administration of a therapeutically effective amount of a radiosensitizing agent to a patient in order to sensitize neoplastic or cancerous cells and tissue to radiation. As used herein, the term "radiosensitizing agent" which may be read also as a "radiosensitizer" denotes an agent having an effect of enhancing the sensitivity of cancerous and/or neoplastic cells to radiation.

Preferably, the radiosensitizing agents described herein include halogenated nucleosides and their analogs. For example, radiosensitizing agents described herein include 5-iodo-2'-deoxyuridine (IUdR) and prodrugs thereof. 5-iodo-2-pyrimidinone-2'-deoxyribose (IPdR) represents a specific IUdR prodrug. Certain additional halogenated nucleosides that may be used in accordance with the invention include one or more PdR analogs described in U.S. Pat. No. 5,728,684, the entirety of which is incorporated herein by reference. In a preferred aspect, the radiosensitizing agent described herein is IUdR.

The agents utilized in the invention may be administered as such, or in a form from which the active agent can be derived, such as a prodrug. A "prodrug" is a derivative of a compound described herein, the pharmacologic action of which results from the conversion by chemical or metabolic processes in vivo to the active compound. For instance, as set forth herein, IPdR is a prodrug of IUdR. Prodrugs may include compounds wherein an amino acid residue, or a polypeptide chain of two or more (e.g., two, three or four) amino acid residues is covalently joined through an amide or ester bond to a free amino, hydroxyl or carboxylic acid group of the radiosensitizing agent or radiomimetic therapeutic agent. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Prodrug esters as employed herein includes esters and carbonates formed by reacting one or more hydroxyls of compounds of the method described herein with alkyl, alkoxy, or aryl substituted acylating agents employing procedures known to persons having ordinary skill in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., IPdR to IUdR) is a prodrug within the scope and spirit of the invention.

Referring to certain radiosensitizing agents described herein more specifically, IUdR and IPdR (a prodrug of IUdR) are particularly preferred agents. IUdR (5-iodo-2'-deoxyuridine) is a halogenated thymidine analog that is an effective in vitro and in vivo radiosensitizer. The % IUdR-DNA cellular replacement correlates directly with the extent of radiosensitization. While IUdR has been found to be a clinically active radiosensitizer, it requires prolonged continuous intra-arterial or intravenous infusions prior to or during radiation therapy to optimize tumor radiosensitization. However, prolonged continuous infusion presents a challenge in the setting of outpatient radiation therapy and results in myelosuppression and acute GI toxicities that limit the dose and duration of IUdR treatment.

Administering a radiosensitizing agent, a TPI, and/or a radiomimetic agent disclosed herein may be accomplished by any means known to a person skilled in the art. The radiosensitizing agents (or optional radiomimetic therapeutic agents) used in practicing the methods described herein may be administered in an amount sufficient to induce the desired therapeutic effect in the recipient thereof. Thus, the term "therapeutically effective amount" as used herein refers to an amount of the agent which is sufficient to (1) sensitize the cancerous and/or neoplastic cells and tissues to radiation; and/or (2) bring about a detectable therapeutic, preventative, or ameliorative effect (e.g., reduce the quantity of cancerous and/or neoplastic cells). For example, the therapeutically effective amount of a radiosensitizing agent may be that amount that enhances the inhibitory or damaging effect of radiation on cancer cells by at least 10%, at times by at least 20%, 30%, 40%, 50%, 60%, 70% 80%, 90% and even at times by 99-100% of the inhibitory or damaging effect of the radiation on the cancer cells as compared to the effect of radiation of the same cancerous and/or neoplastic cells, without sensitization. Moreover, the magnitude of radiosensitization may be correlated directly to the false incorporation of radiosensitizing agent into suspect DNA. For example, radiosensitization may be correlated directly with the % IUdR-DNA cellular replacement. In fact, the determination of % IUdR-DNA incorporation can serve as a radiosensitization biomarker during treatment.

The radiosensitizing agents described herein may be administered in one or more doses, at least a portion thereof being given to the patient prior to the patient's exposure to radiation. When a treatment schedule involves administration of several doses of the agent, the doses may be the same or different, for example, escalating or de-escalating amounts per administration. In addition, when referring to a radiosensitizing agent it should be understood as also encompassing a combination of such agents.

The radiosensitizing agents described herein are applicable for treating disease in any mammal. Exemplary mammals included laboratory animals, including rodents such as mice, rats and guinea pigs; farm animals such as cows, sheep, pigs and goats; pet animals such as dogs and cats; and primates such as monkeys, apes, and humans. The compounds used in the methods described herein are preferably used in the human treatments.

In conjunction with the radiosensitizing agents, the methods described herein further include the delivery of a compound that inhibits thymidine phosphorylase. As described herein, IUdR may be degraded in vivo by the enzyme thymidine phosphorylase. Therefore, in order to prolong the IUdR half-life in vivo and inhibit a primary route of degradation, the invention may include delivering a thymidine phosphorylase inhibitor to a patient in conjunction with one or more radiosensitizing agents that are metabolized by thymidine phosphorylase, such as IUdR and its prodrug, IPdR. The route of IUdR metabolism by thymidine phosphorylase is shown in FIG. 1. In certain embodiments, the thymidine phosphorylase inhibitor (TPI) may be Tipiracil (i.e., 5-chloro-6-(1-(2-iminopyrrolidinyl)methyl)uracil hydrochloride). Certain thymidine phosphorylase inhibitors, including Tipiracil, and uses thereof, are described in U.S. Pat. Nos. 5,744,475; 6,159,969; 6,294,535; and 7,799,783; the entirety of which are incorporated herein by reference. Accordingly, a "selected effective amount" of a TPI may be defined as an amount delivered to a patient in conjunction with a radiosensitizing agent that is effective to detectably prevent, hinder, or otherwise inhibit metabolic degradation of the radiosensitizing agent as compared to administration of the radiosensitizing agent in the absence of the selected effective amount of the TPI. For example, the radiosensitizing agent and TPI may be administered in a molar ratio of about 1.0:0.5, respectively.

The method may further include irradiating a selected tissue of the patient before, during, and/or after a radiation sensitizing agent has been administered to the patient. Regarding the application of radiation (i.e., "radiation therapy") to the patient or subject more generally, such therapy may encompass any ionizing radiation known to those having ordinary skill in the art. Generally, radiation therapy, and in particular ionizing radiation includes applying to a selected tissue, such as a selected tissue comprising cancerous and/or neoplastic cells, a dose of ionizing radiation or two or more fractions of ionizing radiation. The ionizing radiation is defined as an irradiation dose which is determined according to the disease's characteristics at the selected tissue and therapeutic decision of a physician. The term "fractionated dose(s)" may include, for example, conventional fractionation, hyperfractionation, hypofractionation, and accelerated fractionation. The amount of radiation and doses thereof should be sufficient to damage the highly proliferating cells' genetic material, making it impossible for the irradiated cells to continue growing and dividing.

The fractionated irradiation may vary from daily doses (e.g., one or more times per day) given for a period of weeks, or to once weekly doses given for a period of weeks or months, Radiation may be applied in dosages of about 1 Gy to about 100 Gy, or about 20 to about 80 Gy, or about 30 to 60 Gy.

The dosage in certain embodiments is fractionated, which means that, from about 0.1 to about 10 Gy or from about 1 Gy to about 5 Gy or from about 1 Gy to about 3 Gy are applied in a single session which is repeated several times over the course of about 1 to 10 weeks, or preferably about 2 to 5 weeks. In a certain aspect, the radiation dose may be about 30 to 60 Gy at 1 to 3 Gy fractions over a period of about 2 to 5 weeks.

Additionally, the cancers treated by the methods and compositions described herein may include certain pediatric cancers that are treated in the field with limited doses of radiation. Such pediatric cancers include one or more of leukemia, lymphoma, Hodgkin's disease, rhabdomyosarcoma, Ewing's sarcoma, osteosarcoma and other pediatric soft tissue sarcomas, dysgerminomas, Wilm's tumor, retinoblastoma, ependymoma, and medulloblastoma. Typically, radiation fields that encompass growing bones and tissues need to be limited to levels that will not impair growth in growing children. For example, doses of 1080 cGy are given for neuroblastoma, 1500 to 1800 cGy for lymphomas, 2400 cGy for cranial and 1800 cGy for spinal radiation therapy in CNS leukemias. The administration of such radiation levels would be understood by a person having ordinary skill in the art in light of the present specification.

In some embodiments, the radiosensitizing agents and/or thymidine phosphorylase inhibitors (TPIs) used in the methods described herein may be administered at a dose as described herein. Such doses may be provided in one or more applications per day to produce a desired result. For example, radiosensitizing agents and thymidine phosphorylase inhibitors described herein may be administered once or twice daily at a dose as described herein.

In some embodiments, the radiosensitizing agents and/or thymidine phosphorylase inhibitors (TPIs) used in the methods described herein may be administered at a dose in a range from about 0.01 mg/M$^2$ to about 5000 mg/M$^2$. A dose of from 0.1 to 3000 mg/M$^2$, or from 100 to 2000 mg/M$^2$ in one or more applications per day may be effective to produce a desired result. For example, radiosensitizing agents described herein may be administered once or twice daily at a dose in a range of about 0.01 to 3000 mg/M$^2$. Indeed, radiosensitizing agents described herein (e.g., IPdR) may be administered at a dose in a range from about 1500 to 2000 mg/M$^2$.

In some embodiments, a dose (mg/kg) of the thymidine phosphorylase inhibitor (i.e., Tipiracil) may be greater than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% of a dose (mg/kg) of the radiosensitizing agent (e.g., IPdR or IUdR) when the thymidine phosphorylase inhibitor and the radiosensitizing agent are delivered in combination to a patient, as described herein.

In some embodiments, a dose (mg/kg) of the thymidine phosphorylase inhibitor (i.e., Tipiracil) may be less than 1%, 2%, 3%, 4%, 5%, 6%, 7%, 8%, 9%, 10%, 11% % 2%, 3%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% of a dose (mg/kg) of the radiosensitizing agent (e.g., IPdR or IUdR) when the thymidine phosphorylase inhibitor and the radiosensitizing agent are delivered in combination to a patient, as described herein.

In some embodiments, a dose (mg/kg) of the thymidine phosphorylase inhibitor (i.e., Tipiracil) may be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, $2^5$%, $2^6$%, $2^7$%, $2^8$%, $2^9$%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, $5^3$%, $5^4$%, 55%, $5^6$%, 57%, $5^8$%, $5^9$%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% of a dose (mg/kg) of the radiosensitizing agent (e.g., IPdR or IUdR) when the thymidine phosphorylase inhibitor and the radiosensitizing agent are delivered in combination to a patient, as described herein.

In some embodiments, a dose (mg/kg) of the thymidine phosphorylase inhibitor (i.e., Tipiracil) may be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% of a dose (mg/kg) of the radiosensitizing agent (e.g., IPdR or IUdR) when the thymidine phosphorylase inhibitor and the radiosensitizing agent are delivered in combination to a patient, as described herein.

In some embodiments, a dose of the radiosensitizing agent (e.g., IPdR or IUdR) may be greater than 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 mg/kg.

In some embodiments, a dose of the radiosensitizing agent (e.g., IPdR or IUdR) may be less than 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 mg/kg.

In some embodiments, a dose of the radiosensitizing agent (e.g., IPdR or IUdR) may be about 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 mg/kg.

In some embodiments, a dose of the radiosensitizing agent (e.g., IPdR or IUdR) may be 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 mg/kg.

In some embodiments, a dose of the thymidine phosphorylase inhibitor (i.e., Tipiracil) may be greater than 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg.

In some embodiments, a dose of the thymidine phosphorylase inhibitor (i.e., Tipiracil) may be less than 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg.

In some embodiments, a dose of the thymidine phosphorylase inhibitor (i.e., Tipiracil) may be about 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg.

In some embodiments, a dose of the thymidine phosphorylase inhibitor (i.e., Tipiracil) may be 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg.

In some embodiments, a dose of the thymidine phosphorylase inhibitor (i.e., Tipiracil) may be 0.1 to 100 mg/kg, or 1 to 50 mg/kg.

Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the agents in a bioassay (either in vitro or in vivo), and thus establish the appropriate dosage to be administered.

In general, the agents used in the methods described herein can be administered to provide radiosensitization as set forth above using any acceptable route known in the art, either alone or in combination with one or more TPIs or other therapeutic agents as pharmaceutical compositions with a physiologically compatible carrier medium. Thus, the agent(s) described herein can be administered orally, parenterally, such as by intravenous or intraarterial infusion, intramuscular, intraperitoneal, intrathecal or subcutaneous injection, by liposome-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. In some embodiments, an orally administered dosage unit may include a radiosensitizing agent and a thymidine phosphorylase inhibitor. In some embodiments, an orally administered dosage unit may include a radiosensitizing agent, a thymidine phosphorylase inhibitor, and a radiomimetic therapeutic agent. For example, an orally administered dosage unit may be a multi-component tablet (e.g., a multilayer tablet) having one or more components where each component may be composed of a radiosensitizing agent, a thymidine phosphorylase inhibitor, a radiomimetic therapeutic agent, or a combination thereof. Indeed, a multi-component tablet may have an inner component (e.g., a core) and an outer component (e.g., a coating layer or shell) where the outer component may be dissolved or degraded to release a first agent and the inner component may then be dissolved or degraded to release a second agent. Certain pharmaceutical compositions described herein may be prepared as solid dosage forms that include a multi-component or multi-layer tablet. The multi-component tablet may have an inner component (e.g., a core) that includes a radiosensitizing agent (e.g., IUdR or IPdR) and a first physiologically compatible carrier medium; and an outer component (e.g., a coating layer or shell) disposed around the inner component that includes a thymidine phosphorylase inhibitor (e.g., Tipiracil) and a second physiologically compatible carrier medium. The first and second physiologically compatible carrier mediums may be the same or different.

Suitable dosage forms for parenteral administration include injectable solutions or suspensions, suppositories, powder formulations, such as microcrystals or aerosol spray. The active agents of the invention may also be incorporated into a conventional transdermal delivery system.

As used herein, the expression "physiologically compatible carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20$^{th}$ edition, A. R. Genaro et al., Part 5, Pharmaceutical Manufacturing, pp. 669-1015 (Lippincott Williams & Wilkins, Baltimore, MD/Philadelphia, PA) (2000) discloses various carriers used in formulating pharmaceutical compositions and known techniques for the preparation thereof. Except insofar as any conventional pharmaceutical carrier medium is incompatible with either the radiosensitizing, TPI, or radiomimetic therapeutic agents described herein, such as by producing an undesirable biological effect or otherwise interacting in an deleterious manner with any other component(s) of a formulation comprising such compounds or agents, its use is contemplated to be within the scope of this invention.

For the production of solid dosage forms, including hard and soft capsules, the agents described herein may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. Pharmaceutical compositions or formulations may also contain one or more additives including, without limitation, preservatives, stabilizers, e.g., UV stabilizers, emulsifiers, sweeteners, salts to adjust the osmotic pressure, buffers, coating materials and antioxidants.

The invention may further include controlled-release, sustained-release, or extended-release therapeutic dosage forms for administration of the agents described herein, which involve incorporation of the agents into a suitable delivery system. This dosage form controls release of the active agent(s) in such a manner that an effective concentration of the active agent(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the agent.

In pharmaceutical compositions used in practicing a method described herein, the specified agent(s) (e.g., radiosensitizing agent, TPI, and/or radiomimetic therapeutic agent) may be present in an amount of at least 0.5 and generally not more than 95% by weight, based on the total weight of the composition, including carrier medium and/or supplemental active agent(s), if any. Preferably, the proportion of active agent(s) varies between 30-90% by weight of the composition.

The methods described herein may further include the step of surgically resecting a cancerous tissue where the cancerous tissue includes a solid tumor. Resection of the cancerous tissue may be performed before or after at least one of the steps of administering a therapeutically effective amount of a radiosensitizing agent, administering a selected effective amount of a TPI, and applying radiation therapy to the patient. Resection of the solid tumor may allow for the mass to be reduced prior to application of the methods described herein.

In certain optional embodiments, the methods described herein include providing a therapeutically effective amount of a radiomimetic therapeutic agent to the patient. An exemplary radiomimetic therapeutic agent that may be administered in conjunction with the radiosensitizing agents described herein is cis-platinum (i.e., cis-diamminedichloroplatinum).

In accordance with the foregoing methods described herein, a kit is provided that may include a radiosensitizing agent (one or more of such agents), a thymidine phosphorylase inhibitor (TPI) (one or more of such agents), and instructions for use of the radiosensitizing agent and the TPI in combination with radiation therapy for treating cancer or neoplastic disease in a patient in need of such treatment. Optionally, the kits described herein may include one or more radiomimetic therapeutic agents.

The kits described herein may be used in the methods as described herein.

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

EXAMPLES

Example 1: Evaluation of the Pharmacokinetic Profile of IUdR (100 mg/kg) and Tipiracil in Rats Following Single Oral Administration The purpose of this study was to determine the pharmacokinetics parameters of IUdR in male Sprague-Dawley rats following single oral (PO) administration the IUdR (i.e., Compound A) and Tipiracil (i.e., Compound B).

A control formulation was prepared where Compound A was dissolved in 5% DMSO+95% PBS to yield a final concentration of 10 mg/mL for oral administration. The prepared formulation was white suspension (pH~7).

A second formulation was prepared where Compound A and Compound B were dissolved in 5% DMSO+95% PBS to yield a final concentration of 10 mg/mL (Compound A) and 0.79 mg/mL (Compound B) for oral administration. The prepared formulation was white suspension (pH~7).

Animal Acquisition and Assignment to Study. A total of 8 male experimental Sprague-Dawley Rats were transferred from stock colony, and 6 animals were placed on study.

Dose Administration. The test article was administered via a single oral administration. Dose administration information is presented in the following Table 1.

TABLE 1

Dose Administration

| Animal Number | Group Number | Sex | Body Weight (g) | Dose Level (mg/kg) | Dose Conc. (mg/mL)* | Dose Volume (mL/kg) | Volume Administered (mL) | Dose Route** |
|---|---|---|---|---|---|---|---|---|
| 101 | 1 | Male | 186.1 | 100 | 10 | 10 | 1.9 | PO |
| 102 | 1 | Male | 187.2 | 100 | 10 | 10 | 1.9 | PO |
| 103 | 1 | Male | 196.1 | 100 | 10 | 10 | 2.0 | PO |
| 201 | 2 | Male | 204.5 | 100 (A) and 7.9 (B) | 10 (A) and 0.79 (B) | 10 | 2.0 | PO |
| 202 | 2 | Male | 206.3 | 100 (A) and 7.9 (B) | 10 (A) and 0.79 (B) | 10 | 2.1 | PO |
| 203 | 2 | Male | 212.2 | 100 (A) and 7.9 (B) | 10 (A) and 0.79 (B) | 10 | 2.1 | PO |

*The dose was expressed as free form.
**The animals that dosed via orally were fasted overnight (10-16 hrs) prior to oral administration. Notably, food supply to the animals dosed orally were resumed 2 hours post-dose.

Sample Collection and Bioanalysis. Blood samples (approximately 200 μL/sample) were collected via jugular vein at Pre-dose and Post-dose (5 min, 15 min, 30 min, 1 h, 2 h, 4 h, 6 h, 8 h and 24 h). Blood samples were placed into tubes containing $K_2$EDTA and centrifuged conditions at 8000 rpm for 6 minutes at 2-8° C. to separate plasma from the samples. Following centrifugation, the resulting plasma were transferred to clean tubes and stored frozen at −80° C. pending bioanalysis.

Pharmacokinetic Analysis. The PK analysis and interpretation of the results were conducted by Medicilon Preclinical Research (Shanghai) LLC. A non-compartmental module of WinNonlin® Professional was used to calculate parameters. Any BLQs (LLOQ=10.0 ng/mL for Compound A) were omitted when calculate the PK parameters.

Clinical Observations. No abnormal observations were noted.

Figure 2A:
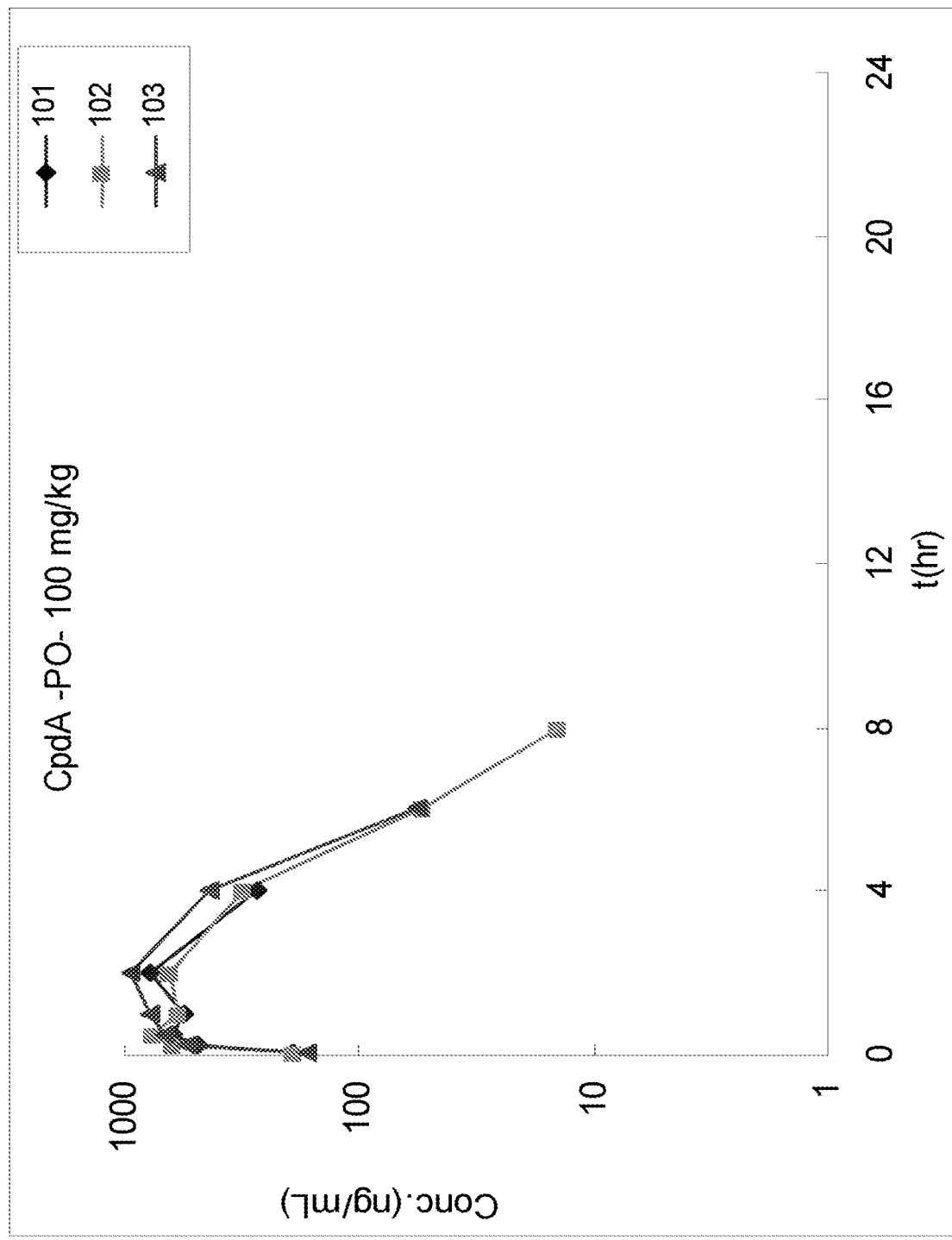
FIGS. 2A to 2C illustrate log-linear plots of plasma concentration of IUdR in rats following oral administration of IUdR at 100 mg/kg without Tipiracil (FIG. 2A) and with Tipiracil at 7.9 mg/kg (FIG. 2B).
Figure 2B:
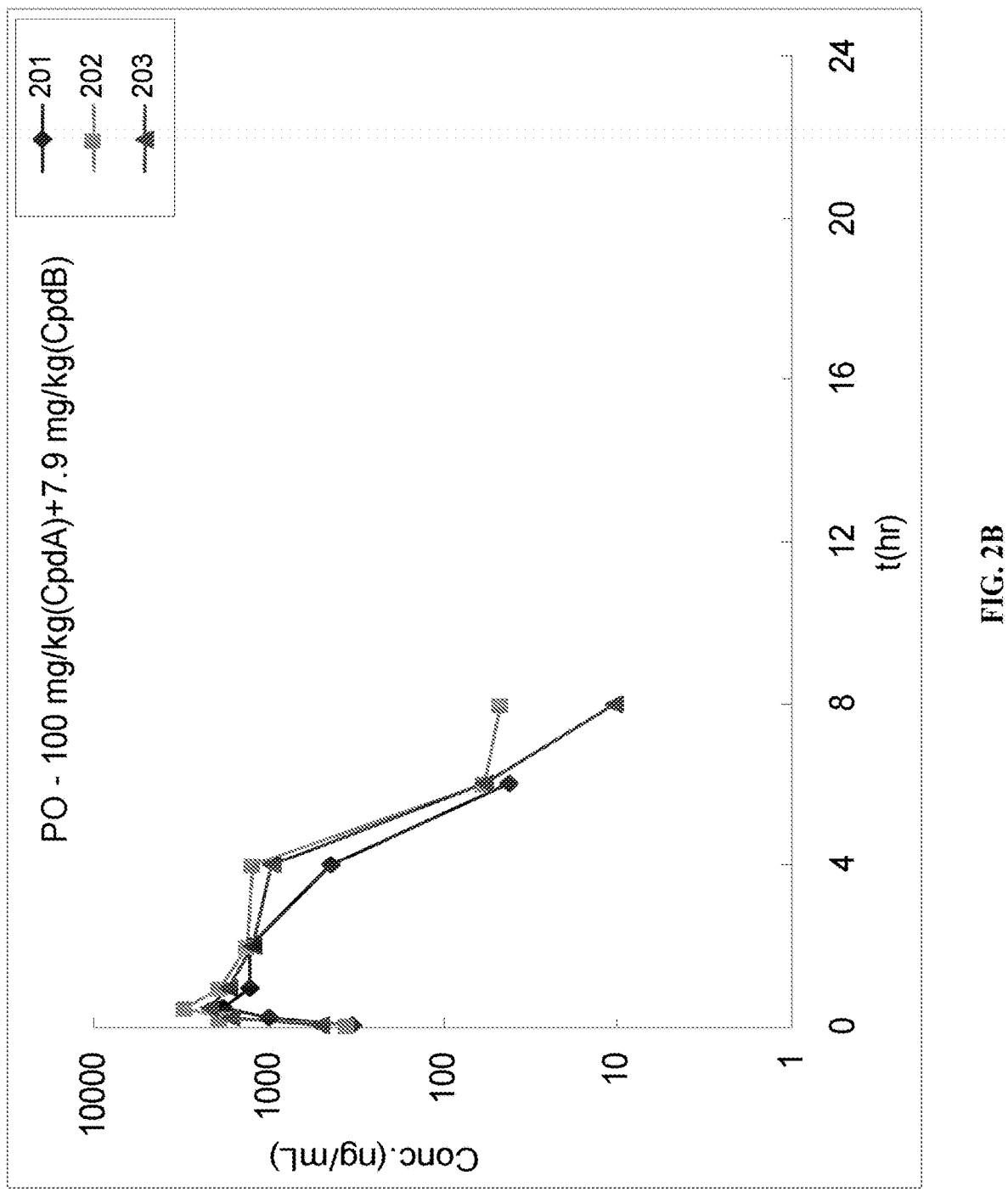
Figure 2C:
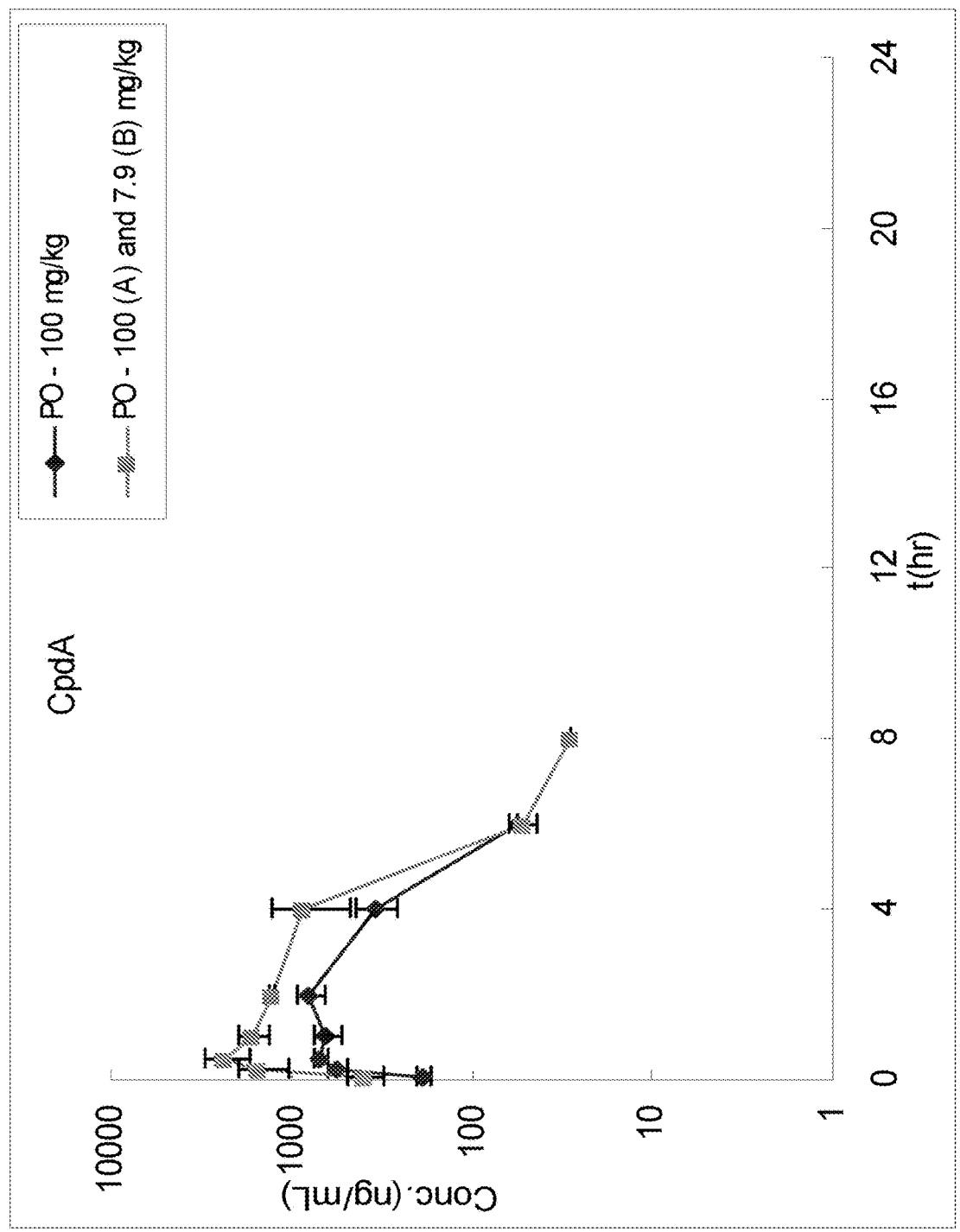

Results. The results of the study are provided in Tables 2 to 4 and FIGS. 2A to 2C.

TABLE 2

Plasma concentration of Compound A in rats following oral administration

| Time points (hr) | Plasma Concentration (ng/mL) PO-100 (Compound A) mg/kg | | | | |
|---|---|---|---|---|---|
| | 101 | 102 | 103 | Mean | SD |
| 0 | BLQ | BLQ | BLQ | NA | NA |
| 0.083 | 191.02 | 192.41 | 168.24 | 183.89 | 13.57 |
| 0.25 | 488.90 | 628.30 | 538.67 | 551.95 | 70.64 |
| 0.5 | 627.41 | 755.39 | 684.80 | 689.20 | 64.10 |
| 1 | 555.81 | 596.55 | 772.49 | 641.62 | 115.15 |
| 2 | 773.62 | 645.17 | 943.79 | 787.53 | 149.80 |
| 4 | 276.40 | 316.82 | 441.37 | 344.87 | 85.98 |
| 6 | BLQ | 54.01 | 56.61 | 55.31 | NA |
| 8 | BLQ | 14.06 | BLQ | NA | NA |
| 24 | BLQ | BLQ | BLQ | NA | NA |

| Time points (hr) | PO-100 (Compound A) + 7.9 (Compound B) mg/kg | | | | |
|---|---|---|---|---|---|
| | 201 | 202 | 203 | Mean | SD |
| 0 | BLQ | BLQ | BLQ | NA | NA |
| 0.083 | 333.57 | 349.38 | 503.96 | 395.63 | 94.15 |
| 0.25 | 1000.36 | 1912.16 | 1611.65 | 1508.06 | 464.64 |
| 0.5 | 1826.53 | 3032.67 | 2159.56 | 2339.59 | 622.90 |
| 1 | 1288.97 | 1908.57 | 1671.33 | 1622.96 | 312.62 |
| 2 | 1270.99 | 1309.80 | 1227.78 | 1269.52 | 41.03 |
| 4 | 436.13 | 1238.72 | 950.09 | 874.98 | 406.53 |
| 6 | 42.32 | 57.49 | 56.82 | 52.21 | 8.58 |
| 8 | BLQ | 46.41 | 10.58 | 28.50 | NA |
| 24 | BLQ | BLQ | BLQ | NA | NA |

LLOQ = 10 ng/mL for plasma
SD: Standard deviation
NA: Not applicable.
BLQ: Below Limit of Quantitation

TABLE 3

Selected pharmacokinetics parameters of Compound
A in rats following oral administration

| Animal Number | $t_{1/2}$ h | $T_{max}$ h | $C_{max}$ ng/mL | $AUC_{(0-t)}$ ng/mL*h | $AUC_{(0-\infty)}$ ng/mL*h | $MRT_{(0-\infty)}$ h |
|---|---|---|---|---|---|---|
| PO-20 (Compound A) mg/kg | | | | | | |
| 101 | NA | 2.00 | 773.62 | 2214.79 | NA | NA |
| 102 | 0.89 | 0.50 | 755.39 | 2609.22 | 2627.28 | 2.29 |
| 103 | NA | 2.00 | 943.79 | 3324.55 | NA | NA |
| Mean | NA | 1.50 | 824.27 | 2716.19 | NA | NA |
| SD | NA | 0.87 | 103.91 | 562.56 | NA | NA |
| PO-20 (Compound A) + 7.9 (Compound B) mg/kg | | | | | | |
| 201 | 0.81 | 0.50 | 1826.53 | 4723.01 | 4772.76 | 1.94 |
| 202 | 1.17 | 0.50 | 3032.67 | 7614.57 | 7692.59 | 2.31 |
| 203 | 0.62 | 0.50 | 2159.56 | 6328.43 | 6337.84 | 2.19 |
| Mean | 0.87 | 0.50 | 2339.59 | 6222.01 | 6267.73 | 2.15 |
| SD | 0.28 | 0.00 | 622.90 | 1448.71 | 1461.18 | 0.19 |

TABLE 4

Comparison of selected pharmacokinetic parameters
of Compound A in rats following oral administration

| Test Article | $C_{max}$ ng/mL | $AUC_{(0-t)}$ ng/mL * h | $C_{max}$ Ratio | $AUC_{(0-t)}$ Ratio |
|---|---|---|---|---|
| Compound A | 824.27 | 2716.19 | — | — |
| Compound A + B | 2339.59 | 6222.01 | 2.84 | 2.29 |

Compound A) and Tipiracil (i.e., Compound B), with a 100 mg/kg IUdR dose, demonstrated a more than two-fold increase IUdR concentration in the blood following oral administration as compared to IUdR alone.

Example 2: Evaluation of Pharmacokinetic Profile of IUdR (20 mg/kg) and Tipiracil in Rats Following Single Oral Administration The purpose of this study was to determine the pharmacokinetics parameters of IUdR in male Sprague-Dawley rats following single oral (PO) administration the IUdR (i.e., Compound A) and Tipiracil (i.e., Compound B).

A control formulation was prepared where Compound A was dissolved in 5% DMSO+95% PBS to yield a final concentration of 2 mg/mL for oral administration. The prepared formulation was colorless clear solution (pH~8).

A second formulation was prepared where Compound A and Compound B were dissolved in 5% DMSO+95% PBS to yield a final concentration of 2 mg/mL (Compound A) and 0.79 mg/mL (Compound B) for oral administration. The prepared formulation was colorless clear solution (pH~7).

Animal Acquisition and Assignment to Study. A total of 8 male experimental Sprague-Dawley Rats were transferred from stock colony, and 6 animals were placed on study.

Dose Administration. The test article was administered via a single oral administration. Dose administration information is presented in the following Table 5.

TABLE 5

Dose Administration

| Animal Number | Group Number | Sex | Body Weight (g) | Dose Level (mg/kg) | Dose Conc. (mg/mL)* | Dose Volume (mL/kg) | Volume Administered (mL) | Dose Route** |
|---|---|---|---|---|---|---|---|---|
| 101 | 1 | Male | 233.2 | 20 | 2 | 10 | 2.3 | PO |
| 102 | 1 | Male | 223.5 | 20 | 2 | 10 | 2.2 | PO |
| 103 | 1 | Male | 219.8 | 20 | 2 | 10 | 2.2 | PO |
| 201 | 2 | Male | 226.0 | 20 (A) and 7.9 (B) | 2 (A) and 0.79(B) | 10 | 2.3 | PO |
| 202 | 2 | Male | 212.0 | 20 (A) and 7.9 (B) | 2 (A) and 0.79(B) | 10 | 2.1 | PO |
| 203 | 2 | Male | 228.1 | 20 (A) and 7.9 (B) | 2 (A) and 0.79(B) | 10 | 2.3 | PO |

*The dose was expressed as free form.
**The animals that dosed via orally were fasted overnight (10-16 hrs) prior to oral administration. Notably, food supply to the animals dosed orally were resumed 2 hours post-dose.

Sample Collection and Bioanalysis. Blood samples (approximately 200 μL/sample) were collected via jugular vein at Pre-dose and Post-dose (5 min, 15 min, 30 min, 1 h, 2 h, 4 h, 6 h, 8 h and 24 h). Blood samples were placed into tubes containing $K_2$EDTA and centrifuged conditions at 8000 rpm for 6 minutes at 2-8° C. to separate plasma from the samples. Following centrifugation, the resulting plasma were transferred to clean tubes and stored frozen at −80° C. pending bioanalysis.

Pharmacokinetic Analysis. The PK analysis and interpretation of the results were conducted by Medicilon Preclinical Research (Shanghai) LLC. A non-compartmental module of WinNonlin® Professional was used to calculate parameters. Any BLQs (LLOQ=5.0 ng/mL for Compound A) were omitted when calculate the PK parameters.

Clinical Observations. No abnormal observations were noted.

Figure 3A:
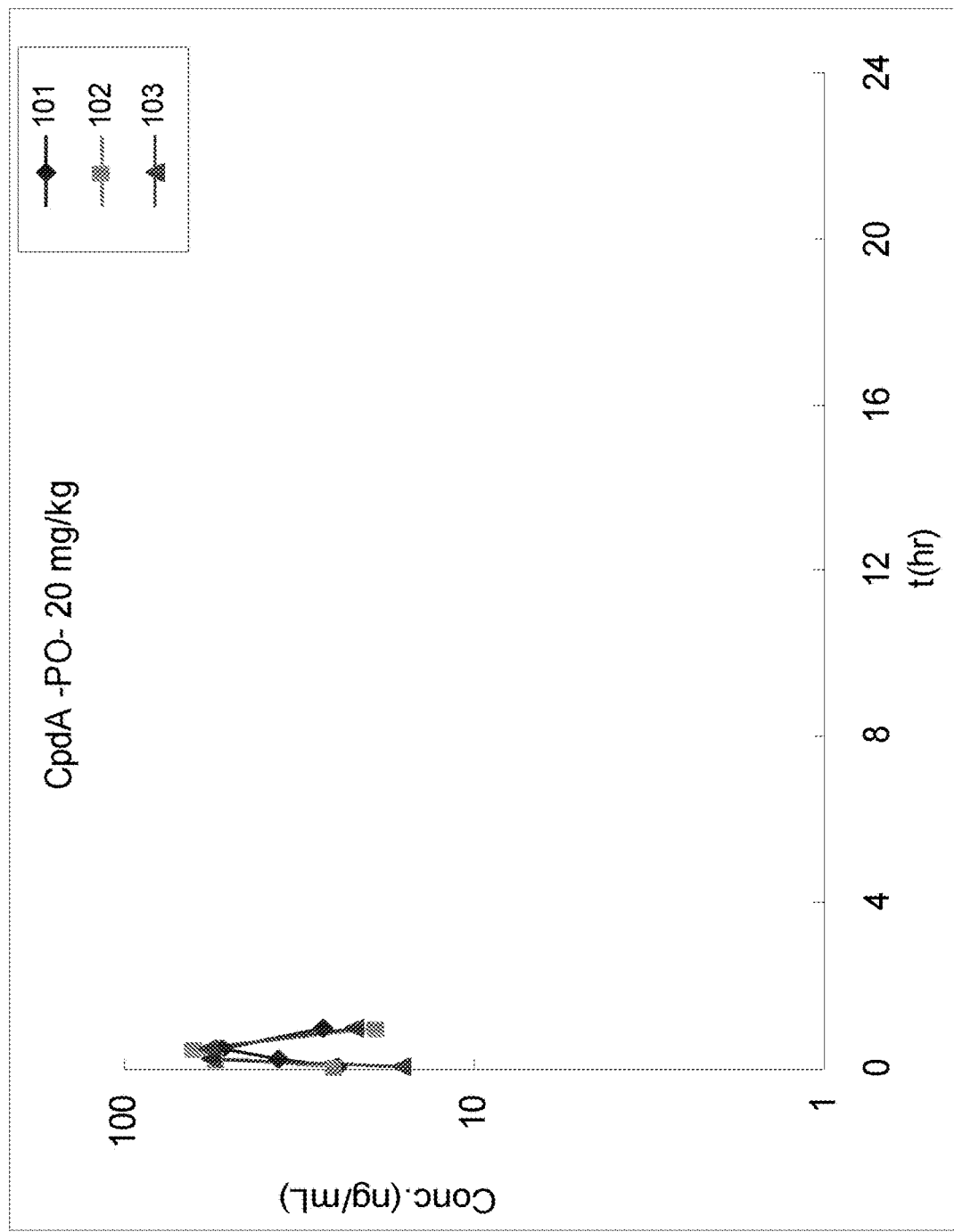
FIGS. 3A to 3C illustrate log-linear plots of plasma concentration of IUdR in rats following oral administration of IUdR at 20 mg/kg without Tipiracil (FIG. 3A) and with Tipiracil at 7.9 mg/kg (FIG. 3B).
Figure 3B:
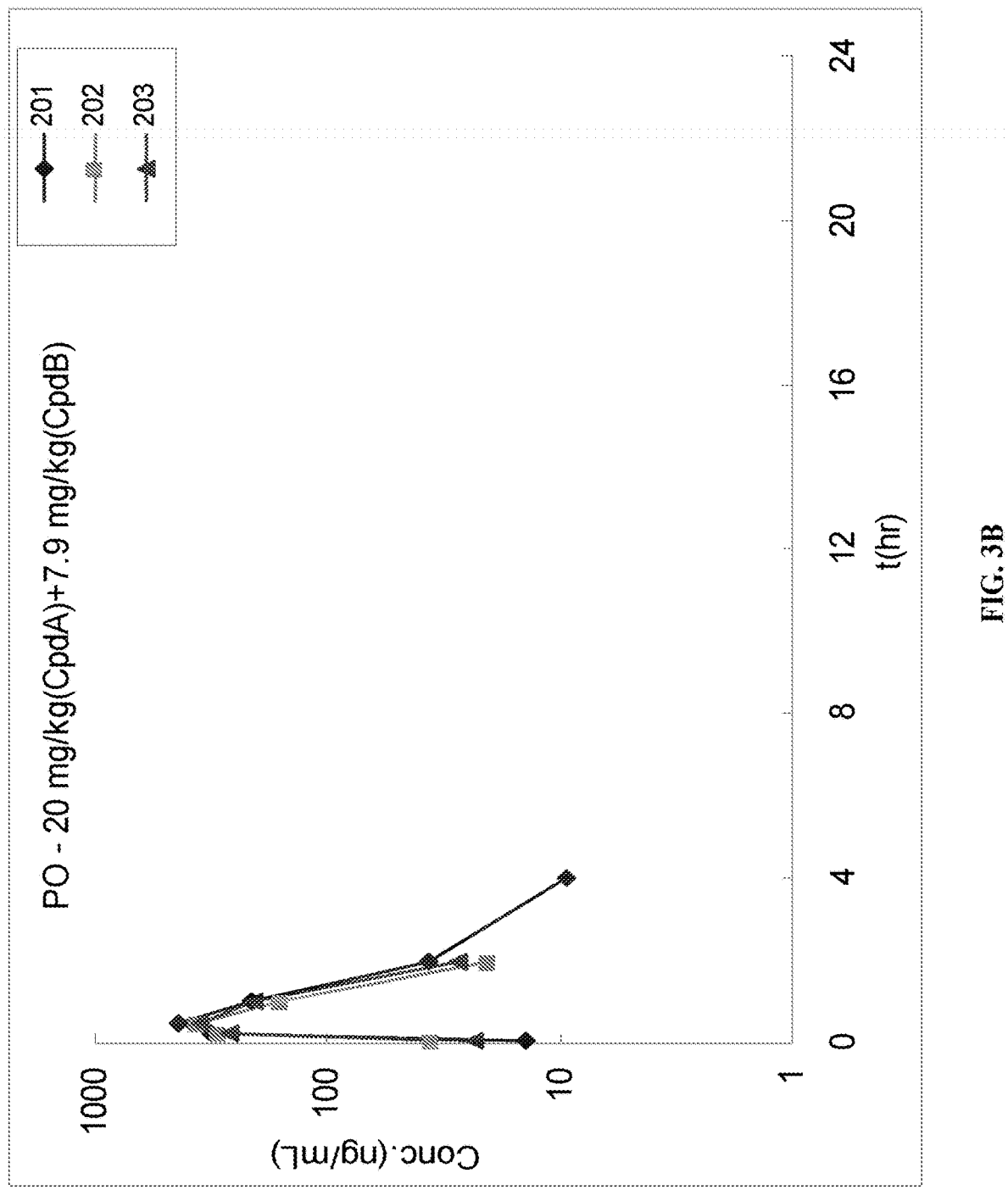
Figure 3C:
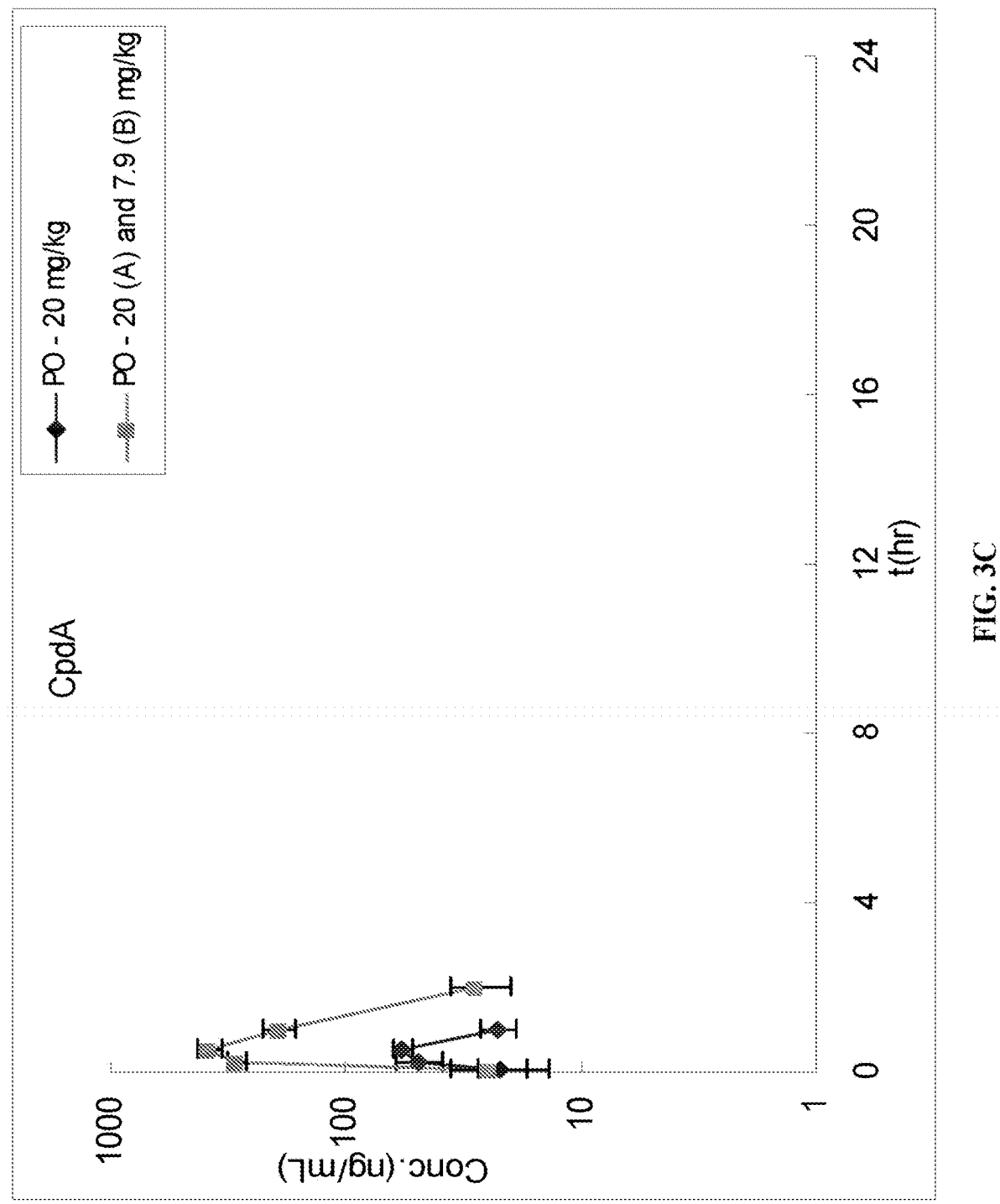

Results. The results of the study are provided in Tables 6 to 8 and FIGS. 3A to 3C.

TABLE 6

Plasma concentration of Compound A in rats following oral administration

| Time points (hr) | Plasma Concentration (ng/mL) PO-20 (Compound A) mg/kg | | | | |
|---|---|---|---|---|---|
| | 101 | 102 | 103 | Mean | SD |
| 0 | BLQ | BLQ | BLQ | NA | NA |
| 0.083 | 24.53 | 25.16 | 16.04 | 21.91 | 5.09 |
| 0.25 | 36.46 | 54.67 | 56.48 | 49.20 | 11.08 |
| 0.5 | 52.45 | 63.23 | 57.34 | 57.67 | 5.39 |
| 1 | 27.25 | 19.19 | 21.93 | 22.79 | 4.10 |
| 2 | BLQ | BLQ | BLQ | NA | NA |
| 4 | BLQ | BLQ | BLQ | NA | NA |
| 6 | BLQ | BLQ | BLQ | NA | NA |
| 8 | BLQ | BLQ | BLQ | NA | NA |
| 24 | BLQ | BLQ | BLQ | NA | NA |

| Time points (hr) | PO-20 (Compound A) + 7.9 (Compound B) mg/kg | | | | |
|---|---|---|---|---|---|
| | 201 | 202 | 203 | Mean | SD |
| 0 | BLQ | BLQ | BLQ | NA | NA |
| 0.083 | 14.12 | 36.03 | 23.44 | 24.53 | 11.00 |
| 0.25 | 321.36 | 290.22 | 261.33 | 290.97 | 30.02 |
| 0.5 | 433.57 | 358.18 | 354.27 | 382.01 | 44.70 |
| 1 | 212.44 | 158.83 | 209.52 | 193.60 | 30.14 |
| 2 | 36.37 | 20.49 | 27.20 | 28.02 | 7.97 |
| 4 | 9.38 | BLQ | BLQ | NA | NA |
| 6 | BLQ | BLQ | BLQ | NA | NA |
| 8 | BLQ | BLQ | BLQ | NA | NA |
| 24 | BLQ | BLQ | BLQ | NA | NA |

LLOQ = 5 ng/mL for plasma
SD: Standard deviation
NA: Not applicable.
BLQ: Below Limit of Quantitation

TABLE 7

Selected pharmacokinetics parameters of Compound A in rats following oral administration

| Animal Number | $t_{1/2}$ h | $T_{max}$ h | $C_{max}$ ng/mL | $AUC_{(0-t)}$ ng/mL*h | $AUC_{(0-\infty)}$ ng/mL*h | $MRT_{(0-\infty)}$ h |
|---|---|---|---|---|---|---|
| PO-20 (Compound A) mg/kg | | | | | | |
| 101 | NA | 0.50 | 52.45 | 37.15 | NA | NA |
| 102 | NA | 0.50 | 63.23 | 43.05 | NA | NA |
| 103 | NA | 0.50 | 57.34 | 40.76 | NA | NA |
| Mean | NA | 0.50 | 57.67 | 40.32 | NA | NA |
| SD | NA | 0.00 | 5.39 | 2.98 | NA | NA |
| PO-20 (Compound A) + 7.9 (Compound B) mg/kg | | | | | | |
| 201 | 0.64 | 0.50 | 433.57 | 454.62 | 463.22 | 0.96 |
| 202 | 0.36 | 0.50 | 358.18 | 328.70 | 339.33 | 0.73 |
| 203 | 0.39 | 0.50 | 354.27 | 361.00 | 376.47 | 0.81 |
| Mean | 0.46 | 0.50 | 382.01 | 381.44 | 393.01 | 0.84 |
| SD | 0.15 | 0.00 | 44.70 | 65.40 | 63.58 | 0.12 |

TABLE 8

Selected pharmacokinetics parameters of Compound A in rats following oral administration

| Test Article | $C_{max}$ ng/mL | $AUC_{(0-t)}$ ng/mL * h | $C_{max}$ Ratio | $AUC_{(0-t)}$ Ratio |
|---|---|---|---|---|
| Compound A | 57.67 | 40.32 | — | — |
| Compound A + B | 382.01 | 381.44 | 6.62 | 9.46 |

As shown in the foregoing results, the combination of IUdR (i.e., Compound A) and Tipiracil (i.e., Compound B), with a 20 mg/kg IUdR dose, demonstrated a more than nine-fold increase in IUdR concentration in the blood following oral administration as compared to IUdR alone.

Example 3: Comparison of 20 mg/kg and 100 mg/kg IUdR Doses with and without Tipiracil from Examples 1 and 2

Figure 4:
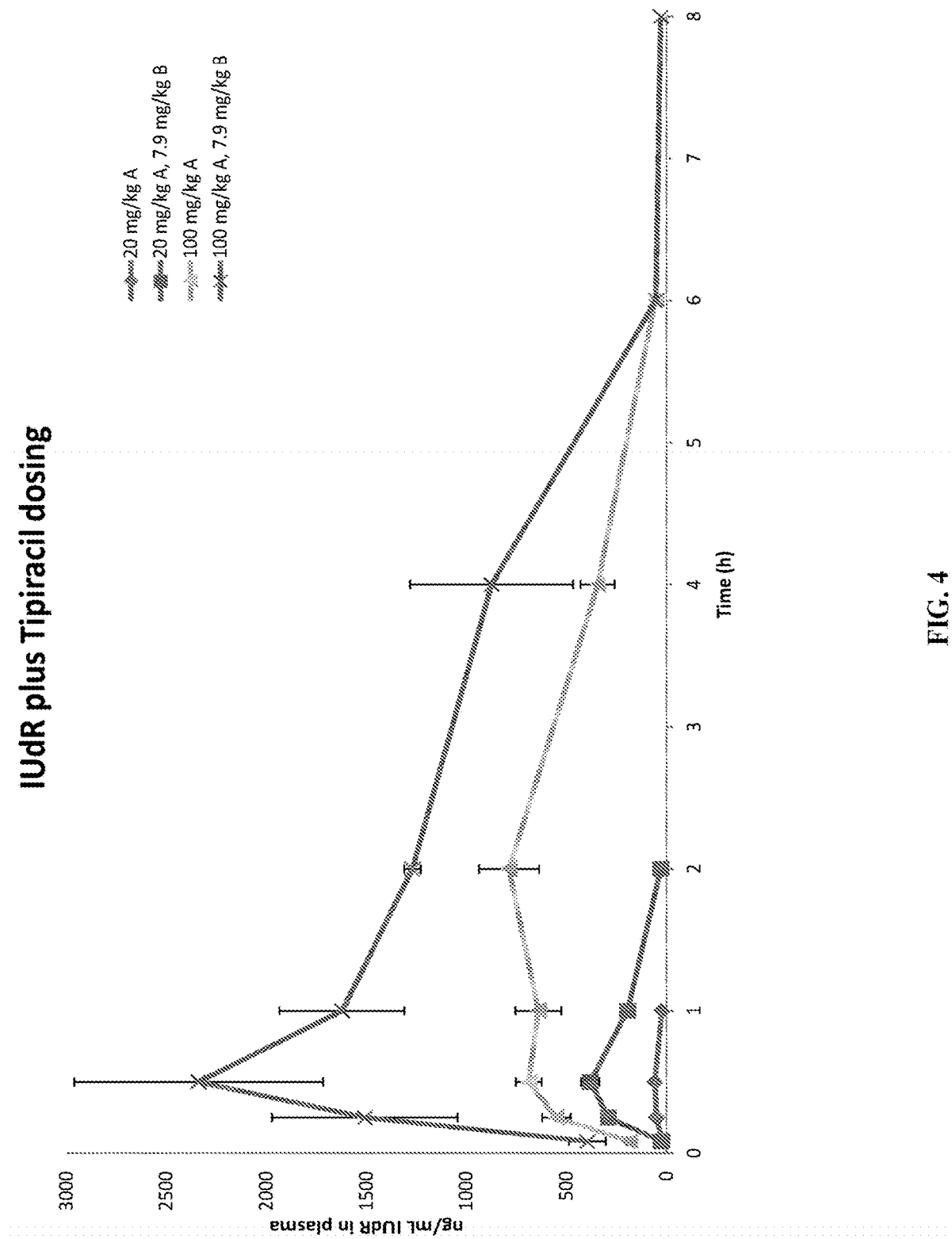
FIG. 4 illustrates the difference in plasma concentration of IUdR in rats following oral administration of IUdR at 100 mg/kg and 20 mg/kg with and without Tipiracil. Compound A=IUdR, Compound B=Tipiracil.

The animal data provided in Examples 1 and 2 may be compared as shown in FIG. 4.

A number of patent and non-patent publications are cited herein in order to describe the state of the art to which this invention pertains. The entire disclosure of each of these publications is incorporated by reference herein.

While certain embodiments of the invention have been described and/or exemplified above, various other embodiments will be apparent to those skilled in the art from the foregoing disclosure. The invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All methods, kits, compositions, formulations, and other embodiments described herein that embody the invention can, in alternate embodiments, be more specifically defined by any of the transitional terms "comprising," "consisting essentially of," and "consisting of."

REFERENCES

1. Vallerga A K, Zarling D A, Kinsella T J. New radiosensitizing regimens, drugs, prodrugs, and candidates. Clin Adv Hematol Oncol. 2004; 2(12):793-805.
2. Krishnamurthi S S, Seo Y, Kinsella T J. Adjuvant therapy for rectal cancer. Clin Colon Rectal Surg. 2007; 20(3): 167-81. PMCID: 2789506.
3. Gerard J P, Azria D, Gourgou-Bourgade S, Martel-Laffay I, Hennequin C, Etienne P L, et al. Comparison of two neoadjuvant chemoradiotherapy regimens for locally advanced rectal cancer: results of the phase III trial ACCORD 12/0405-Prodige 2. J Clin Oncol. 2010; 28(10):1638-44.
4. Aschele C, Cionini L, Lonardi S, Pinto C, Cordio S, Rosati G, et al. Primary tumor response to preoperative chemoradiation with or without oxaliplatin in locally advanced rectal cancer: pathologic results of the STAR-01 randomized phase III trial. J Clin Oncol. 2011; 29(20): 2773-80.
5. Rodel C, Liersch T, Becker H, Fietkau R, Hohenberger W, Hothorn T, et al. Preoperative chemoradiotherapy and postoperative chemotherapy with fluorouracil and oxaliplatin versus fluorouracil alone in locally advanced rectal cancer: initial results of the German CAO/ARO/AIO-04 randomised phase 3 trial. Lancet Oncol. 2012; 13(7):679-87.
6. Roh Y G, O'Connell M J, Beart R W, Pitot H C, Shields A F, Parda D S, Sharif S, Allegra J Petrelli J, Landry J C, Ryan D P, Arora A, Evans T L, Soori G S, Chu L, Landes R V, Mohiuddin M, Lopa S, Wolmark N. The impact of capecitabine and oxaliplatin in the preoperative multimodality treatment in patients with carcinoma of the rectum: NSABP R-04. Journal of Clinical Oncology. 2011; 29(15).
7. Kinsella T J. An approach to the radiosensitization of human tumors. Cancer J Sci Am. July-August 1996; 2(4):184-193.
8. Shewach D S, Lawrence T S. Antimetabolite radiosensitizers. J Clin Oncol. Sep. 10, 2007; 25(26):4043-4050.
9. Lawrence T S, Davis M A, Maybaum J, Stetson P L, Ensminger W D. The dependence of halogenated pyrimidine incorporation and radiosensitization on the duration of drug exposure. International journal of radiation oncology, biology, physics. June 1990; 18(6):1393-1398.
10. Fornace A J, Jr., Dobson P P, Kinsella T J. Enhancement of radiation damage in cellular DNA following unifilar substitution with iododeoxyuridine. International journal of radiation oncology, biology, physics. April 1990; 18(4): 873-878.
11. Kinsella T J, Dobson P P, Mitchell J B, Fornace A J, Jr. Enhancement of X ray induced DNA damage by pretreatment with halogenated pyrimidine analogs. International journal of radiation oncology, biology, physics. May 1987; 13(5):733-739.
12. Lawrence T S, Davis M A, Maybaum J, Stetson P L, Ensminger W D. The effect of single versus double-strand substitution on halogenated pyrimidine-induced radiosensitization and DNA strand breakage in human tumor cells. Radiation research. August 1990; 123(2):192-198.
13. Kinsella T J. Coordination of DNA mismatch repair and base excision repair processing of chemotherapy and radiation damage for targeting resistant cancers. Clin Cancer Res. Mar. 15, 2009; 15(6):1853-1859.
14. Kinsella T J. Update on radiosensitization by halogenated thymidine analogs-molecular mechanisms of drug processing and cell death signaling: implications for future clinical trials. Cancer Biol Ther. October 2008; 7(10):1567-1569.
15. Rodriguez R, Ritter M A, Fowler J F, Kinsella T J. Kinetics of cell labeling and thymidine replacement after continuous infusion of halogenated pyrimidines in vivo. International journal of radiation oncology, biology, physics. Apr. 30, 1994; 29(1):105-113.
16. Prados M D, Scott C B, Rotman M, et al. Influence of bromodeoxyuridine radiosensitization on malignant glioma patient survival: a retrospective comparison of survival data from the Northern California Oncology Group (NCOG) and Radiation Therapy Oncology Group trials (RTOG) for glioblastoma multiforme and anaplastic astrocytoma. International journal of radiation oncology, biology, physics. Feb. 1, 1998; 40(3):653-659.
17. Urtasun R C, Kinsella T J, Faman N, DelRowe J D, Lester S G, Fulton D S. Survival improvement in anaplastic astrocytoma, combining external radiation with halogenated pyrimidines: final report of RTOG 86-12, Phase T-TT study. International journal of radiation oncology, biology, physics. Dec. 1, 1996; 36(5):1163-1167.
18. Schulz C A, Mehta M P, Badie B, et al. Continuous 28-day iododeoxyuridine infusion and hyperfractionated accelerated radiotherapy for malignant glioma: a phase I clinical study. International journal of radiation oncology, biology, physics. Jul. 15, 2004; 59(4):1107-1115.
19. Chang A E, Collins J M, Speth P A, et al. A phase I study of intraarterial iododeoxyuridine in patients with colorectal liver metastases. J Clin Oncol. May 1989; 7(5):662-668.
20. Eisbruch A, Robertson J M, Johnston C M, et al. Bromodeoxyuridine alternating with radiation for advanced uterine cervix cancer: a phase I and drug incorporation study. J Clin Oncol. January 1999; 17(1): 31-40.
21. Epstein A H, Lebovics R S, Goffman T, et al. Treatment of locally advanced cancer of the head and neck with 5'-iododeoxyuridine and hyperfractionated radiation therapy: measurement of cell labeling and thymidine replacement. Journal of the National Cancer Institute. Dec. 7, 1994; 86(23):1775-1780.
22. Knol J A, Walker S C, Robertson J M, et al. Incorporation of 5-bromo-2'-deoxyuridine into colorectal liver metastases and liver in patients receiving a 7-day hepatic arterial infusion. Cancer research. Sep. 1, 1995; 55(17): 3687-3691.
23. Groves M D, Maor M H, Meyers C, et al. A phase II trial of high-dose bromodeoxyuridine with accelerated fractionation radiotherapy followed by procarbazine, lomustine, and vincristine for glioblastoma multiforme. International journal of radiation oncology, biology, physics. Aug. 1, 1999; 45(1):127-135.
24. Speth P A, Kinsella T J, Belanger K, et al. Fluorodeoxyuridine modulation of the incorporation of iododeoxyuridine into DNA of granulocytes: a phase I and clinical pharmacological study. Cancer research. May 15, 1988; 48(10):2933-2937.
25. Berry S E, Garces C, Hwang H S, et al. The mismatch repair protein, hMLH1, mediates 5-substituted halogenated thymidine analogue cytotoxicity, DNA incorporation, and radiosensitization in human colon cancer cells. Cancer research. Apr. 15, 1999; 59(8):1840-1845.
26. McGinn C J, Kunugi K A, Tutsch K D, et al. Leucovorin modulation of 5-iododeoxyuridine radiosensitization: a phase I study. Clin Cancer Res. August 1996; 2(8):1299-1305.
27. Berry S E, Davis T W, Schupp J E, Hwang H S, de Wind N, Kinsella T J. Selective radiosensitization of drug-resistant MutS homologue-2 (MSH2) mismatch repair-deficient cells by halogenated thymidine (dThd) analogues: Msh2 mediates dThd analogue DNA levels and the differential cytotoxicity and cell cycle effects of the dThd analogues and 6-thioguanine. Cancer research. Oct. 15, 2000; 60(20):5773-5780.
28. Fink D, Aebi S, Howell S B. The role of DNA mismatch repair in drug resistance. Clin Cancer Res. January 1998; 4(1):1-6.

29. Seo Y, Yan T, Schupp J E, Colussi V, Taylor K L, Kinsella T J. Differential radiosensitization in DNA mismatch repair-proficient and -deficient human colon cancer xenografts with 5-iodo-2-pyrimidinone-2'-deoxyribose. Clin Cancer Res. Nov. 15, 2004; 10(22):7520-7528.

30. Chi K H, et al. Iododeoxyuridine Chemosensitization of cis-Diamminedichloroplatinum(II) in Human Bladder Cells. Cancer Research. May 15, 1994; 54:2701-2706.

What is claimed is:

1. A method for sensitizing cancer cells to radiation therapy in a patient having cancer, the method comprising:
   administering to the patient a therapeutically effective amount of a radiosensitizing agent selected from 5-iodo-2'-deoxyuridine (IUdR) and a prodrug thereof; and
   administering to the patient a selected effective amount of a thymidine phosphorylase inhibitor (TPI), wherein the TPI is Tipiracil;
   wherein the radiosensitizing agent and the TPI are administered in a molar ratio of about 1.0:0.5, respectively.

2. A method for treating cancer in a patient in need thereof, the method comprising:
   administering to the patient a therapeutically effective amount of a radiosensitizing agent selected from 5-iodo-2'-deoxyuridine (IUdR) and a prodrug thereof;
   administering to the patient a selected effective amount of a thymidine phosphorylase inhibitor (TPI), wherein the TPI is Tipiracil; and
   irradiating a selected tissue of the patient, wherein the selected tissue comprises sensitized cancerous cells;
   wherein the radiosensitizing agent and the TPI are administered in a molar ratio of about 1.0:0.5, respectively.

3. The method of claim 1, wherein the radiosensitizing agent is IUdR.

4. The method of claim 1, wherein the radiosensitizing agent is the prodrug 5-iodo-2-pyrimidinone-2'-deoxyribose (IPdR).

5. The method of claim 1, wherein the radiosensitizing agent and the TPI are administered to the patient simultaneously or sequentially.

6. The method of claim 2, wherein the radiosensitizing agent is IUdR.

7. The method of claim 2, wherein the radiosensitizing agent is the prodrug 5-iodo-2-pyrimidinone-2'-deoxyribose (IPdR).

8. The method of claim 2, wherein the radiosensitizing agent and the TPI are administered to the patient simultaneously or sequentially.

9. The method of claim 2, further comprising surgically resecting a selected tissue comprising cancerous cells prior to the administering and the irradiating steps.

10. The method of claim 2, further comprising administering to the patient a therapeutically effective amount of a radiomimetic therapeutic agent.

11. A kit for treating cancer in a patient in need thereof, the kit comprising:
    a radiosensitizing agent selected from 5-iodo-2'-deoxyuridine (IUdR) and a prodrug thereof;
    a thymidine phosphorylase inhibitor (TPI), wherein the TPI is Tipiracil; and
    instructions for administering to the patient a therapeutically effective amount of the radiosensitizing agent and a selected effective amount of the TPI in combination with radiation therapy to irradiate cancerous cells in the patient;
    wherein the radiosensitizing agent and the TPI are in a molar ratio of about 1.0:0.5, respectively.

12. The kit of claim 11, wherein the radiosensitizing agent is IUdR.

13. The kit of claim 11, wherein the radiosensitizing agent is the prodrug 5-iodo-2-pyrimidinone-2'-deoxyribose (IPdR).

14. The kit of claim 11 further comprising a radiomimetic therapeutic agent.

* * * * *